US010179063B2

(12) United States Patent
Frantz et al.

(10) Patent No.: US 10,179,063 B2
(45) Date of Patent: *Jan. 15, 2019

(54) METHOD FOR VACUUM-FORMING DENTAL APPLIANCE

(71) Applicant: Frantz Design Incorporated, Austin, TX (US)

(72) Inventors: Joseph Lee Frantz, Austin, TX (US); Donald Frantz, Austin, TX (US)

(73) Assignee: Frantz Design Incorporated, Austin, TX (US)

( * ) Notice: Subject to any disclaimer, the term of this patent is extended or adjusted under 35 U.S.C. 154(b) by 101 days.

This patent is subject to a terminal disclaimer.

(21) Appl. No.: 14/983,616

(22) Filed: Dec. 30, 2015

(65) Prior Publication Data
US 2016/0106572 A1 Apr. 21, 2016

Related U.S. Application Data

(63) Continuation-in-part of application No. 14/478,511, filed on Sep. 5, 2014, which is a continuation of (Continued)

(51) Int. Cl.
*B29C 51/12* (2006.01)
*B29C 70/70* (2006.01)
(Continued)

(52) U.S. Cl.
CPC .............. *A61F 5/566* (2013.01); *B29C 51/10* (2013.01); *B29C 51/46* (2013.01); *B29C 64/106* (2017.08);
(Continued)

(58) Field of Classification Search
CPC ....... B29C 51/10; B29C 51/12; B29C 64/106; B29C 64/112; B29C 64/118; B29C 69/001; B29C 70/70; B33Y 10/00
(Continued)

(56) References Cited

U.S. PATENT DOCUMENTS 5,947,724 A 9/1999 Frantz
6,109,265 A 8/2000 Frantz
(Continued)

FOREIGN PATENT DOCUMENTS

JP 2009028084 2/2009
WO 2008048649 4/2008
WO 2009155223 12/2009

OTHER PUBLICATIONS

PCT Written Opinion of the International Searching Authority PCT/US2011/030367 dated Nov 11, 2011.

*Primary Examiner* — Leo B Tentoni
(74) *Attorney, Agent, or Firm* — Invention Mine LLC

(57) ABSTRACT

An appliance and methods are described that include embodiments of a mandibular advancement or positioning device which can use elastic bands to pull the jaw forward. The appliance has an upper plastic tray conforming to the patient's upper teeth and including 3D printed sets of retention hooks coupled to the upper plastic tray via being encased in plastic, one on the right and one on the left anterior buccal portion of an upper plastic base. The appliance also has a lower plastic tray conforming to the patient's lower teeth including mandibular dentition, and includes having a 3D printed bite pad which opens the bite vertically. The lower tray also has a set of 3D printed plastic retention hooks encased in plastic extending outwardly from the teeth, one on the right and one on the left of the posterior buccal portion of the lower plastic base. Elastic bands of different lengths and strengths are attached to both the top and bottom retention hooks on both sides of the trays to pull the mandible forward for treatment.

8 Claims, 6 Drawing Sheets

Related U.S. Application Data application No. 13/520,520, filed as application No. PCT/US2011/030367 on Mar. 29, 2011, now Pat. No. 8,882,497.

(60) Provisional application No. 61/318,662, filed on Mar. 29, 2010.

(51) Int. Cl.

| | | |
|---|---|---|
| *A61F 5/56* | (2006.01) | |
| *B29C 51/10* | (2006.01) | |
| *B29C 51/46* | (2006.01) | |
| *B29C 67/00* | (2017.01) | |
| *B29C 69/00* | (2006.01) | |
| *B29C 64/118* | (2017.01) | |
| *B29C 64/112* | (2017.01) | |
| *B29C 64/106* | (2017.01) | |
| *B33Y 10/00* | (2015.01) | |
| *B33Y 30/00* | (2015.01) | |
| *B33Y 50/02* | (2015.01) | |
| *B29K 105/00* | (2006.01) | |
| *B29L 31/00* | (2006.01) | |

(52) U.S. Cl.
CPC .......... *B29C 64/112* (2017.08); *B29C 64/118* (2017.08); *B29C 67/0051* (2013.01); *B29C 67/0088* (2013.01); *B29C 69/001* (2013.01); *B29K 2105/256* (2013.01); *B29L 2031/753* (2013.01); *B33Y 10/00* (2014.12); *B33Y 30/00* (2014.12); *B33Y 50/02* (2014.12)

(58) Field of Classification Search
USPC ....... 264/16, 161, 279.1, 308, 510, 553, 554
See application file for complete search history.

(56) References Cited

U.S. PATENT DOCUMENTS

| | | | |
|---|---|---|---|
| 7,637,262 | B2 | 12/2009 | Bailey |
| 2007/0283967 | A1 | 12/2007 | Bailey |
| 2009/0032030 | A1 | 2/2009 | Callender |
| 2009/0036889 | A1 | 2/2009 | Callender |
| 2013/0095446 | A1* | 4/2013 | Andreiko ................ A61C 7/08 433/6 |
| 2015/0007830 | A1* | 1/2015 | Remmers ................ A61F 5/566 128/848 |

\* cited by examiner

METHOD FOR VACUUM-FORMING DENTAL APPLIANCE

CROSS-REFERENCE TO RELATED APPLICATIONS

An Application Data Sheet (ADS) has been filed on the filing date of this application, it is incorporated by reference herein. Any applications claimed on the ADS for priority under 35 U.S.C. §§ 119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

The present application is related to and/or claims the benefit of the earliest available effective filing date(s) from the following listed application(s) (the "Priority Applications"), if any, listed below (e.g., claims earliest available priority dates for other than provisional patent applications or claims benefits under 35 USC § 119(e) for provisional patent applications, for any and all parent, grandparent, great-grandparent, etc. applications of the Priority Application(s)).

The present application constitutes a continuation-in-part of U.S. patent application Ser. No. 14/478,511 Method and Apparatus for Vacuum-formed Dental Appliance, naming Donald E. Frantz and Joseph Lee Frantz, as inventors filed Sep. 5, 2014, which is currently co-pending or is an application of which a currently co-pending application is entitled to the benefit of the filing date.

Application Ser. No. 14/478,511 constitutes a continuation application of U.S. patent application Ser. No. 13/520,520, now U.S. Pat. No. 8,882,497, Method and Apparatus for Vacuum-formed Dental Appliance, naming Donald E. Frantz and Joseph Lee Frantz, as inventors filed Jul. 3, 2012, which application is entitled to the benefit of the filing date, which application is a nationalization application of PCT/US2011/03067, filed Apr. 21, 2011, pending, which is a non-provisional PCT application of provisional patent application filed Mar. 29, 2010, 61/318,662.

FIELD

This invention related generally to oral appliances for preventing or at least alleviating snoring and sleep apnea.

BACKGROUND OF INVENTION

At the present, there is a need for a viable vacuum formed, non-invasive, inexpensive custom breathing appliance. Most sleep apnea appliances have been made of bulky boil & bite materials. More specifically, there is a need for a dental office manufacturing method utilizing techniques and machines in most dental offices to manufacture a removable mandibular advancement appliance which can use elastic bands to pull the jaw forward and bite pads to open the bite vertically. In addition to the foregoing, other method aspects are described in the claims, drawings, and text forming a part of the present disclosure.

SUMMARY

An embodiment provides a method of making a trial dental appliance for a patient including temporarily attaching a first set of retention hooks to models of the patient's upper teeth; temporarily attaching a set of bite pads integrated with a second set of retention hooks to the model of the patient's lower teeth; vacuum forming sheets of plastic over the models of the patient's upper and lower teeth with the temporarily attached first set of retention hooks and the set of bite pads integrated with the second set of retention hooks in a machine to form upper and lower plastic trays vacuum formed to fit over the teeth of the patient, the heat from the vacuum machine enabling the sheets of plastic to encase the temporarily attached first set of retention hooks and the set of bite pads integrated with the second set of retention hooks; and removing the trays from the models with the incased parts such as hooks and bite pads, which can be 3D printed to be patient specific, the removal of the trays detaching the first set of retention hooks and the set of bite pads integrated with the second set of retention hooks from the models to form the dental appliance to enable attachment of a pair of elastic bands to be placed over the first and second sets of encased retention hooks and bite pads. In addition to the foregoing, other system aspects are described in the claims, drawings, and text forming a part of the present disclosure.

An embodiment provides an oral appliance including upper and lower trays adapted to fit tightly but removably over the occlusal surfaces of the upper and lower teeth of a patient; a first set of retention hooks encased by the upper tray; a set of bite pads integrated with a second set of retention hooks encased by the lower tray to form a bite plane on the occlusal surface of both sides of the lower tray, each bite pad being patient-specific and 3D printed and having a bite surface which protrudes therefrom so as to engage the occlusal surfaces on the upper tray and thus maintain the occlusal surfaces of the trays in predetermined spaced relation, when the trays are so fitted; and means to releasably attach the anterior and posterior portions of both sides of each tray using the first set of retention hooks and the second set of retention hooks to enable a lower jaw to advance forwardly when the upper and lower trays are fitted over the patient's teeth. In addition to the foregoing, other computer program product aspects are described in the claims, drawings, and text forming a part of the present disclosure.

The foregoing is a summary and thus contains, by necessity, simplifications, generalizations and omissions of detail; consequently, those skilled in the art will appreciate that the summary is illustrative only and is not intended to be in any way limiting. Other aspects, features, and advantages of the devices and/or processes described herein, as defined by the claims, will become apparent in the detailed description set forth herein.

BACKGROUND

It is well documented in the literature that an oral appliance that opens the bite and moves the mandible forward will greatly reduce sleep apnea and snoring. It is also documented that these appliances are capable of producing considerable discomfort to patients, unwanted movement of their teeth, and/or tempromandibular joint pain as well as other problems.

A variety of trial oral appliances are available for preventing snoring and sleep apnea. Of these, all are removable, and most advance the mandible, generally do not use elastic bands to move the mandible forward. Bulky "boil & bite" appliances have not been effective and have not had patient acceptance or compliance. These uncomfortable devices have driven patients away from wanting to be treated by a custom oral appliance.

Also, several removable, oral snoring/apnea appliances are adjustable, pulling the jaw forward in different, set percentages of their maximum movement. However, there is a need for patient-specific and adjustable appliances, both in amount of forward movement and vertical opening. Rather than temporary or permanent adjustments to appliances made by either placing spacers, turning screws, or by grinding away plastic or other material, there is a need for patient-specific advancements that do not lock the patient's jaw in one ridged spot causing TMJ pain. In summary, appliances exist in which the amount of advancement may be changed, but the changes result in a new fixed position of the mandible creating pain and discomfort. An appliance is needed that is easily changed vertically or caudally in displacement of the mandible to increase the effectiveness of the appliance.

What is needed is an adjustable oral snoring/sleep apnea appliance which is effective, which has high patient acceptance, and which will not cause temporomandibular joint problems, unwanted tooth movement or soreness.

The appliance of the present disclosure greatly reduces, or eliminates, sleep apnea and snoring, while alleviating temporomandibular joint problems, unwanted tooth movement and soreness, with complete adjustability of the appliance both in the amount of forward movement of the lower jaw, and in the amount of vertical bite opening. Another object is a mandibular advancement appliance with high patient acceptance, comfort, and treatment success. Another object is to make the appliance in a single office visit using machines normally supplied in a typical dentist's office.

DESCRIPTION OF THE DRAWINGS

A better understanding of the subject matter of the application can be obtained when the following detailed description of the disclosed embodiment is considered in conjunction with the following drawings, in which.

DETAILED DESCRIPTION

Embodiments herein relate to methods for manufacturing an oral appliance that requires only a single office visit.

During the office visit, a patient can be fitted for an oral appliance by first obtaining an upper (maxillary) and lower (mandibular) impression of the teeth and supporting soft tissue including the upper hard palate. This impression must be extremely accurate to avoid tooth soreness, and/or movement when the appliance is placed in the patient's mouth. The impression is taken by: (1) having the patient rinse with a pre-impression mouth wash to eliminate any saliva distortion; and (2) pouring the impressions immediately to avoid distortion using a hard lab stone.

In an alternate embodiment, instead of taking impressions, a patient can be visually examined with high definition optics capable of generating 3D images and Computer Aided Design (CAD) images. For example, 3D x-rays can be converted to CAD images that accurately portray the same information that impressions could produce. Due to the speed at which CAD images can be collected, it is possible that CAD images are more accurate than the impressions requiring prolonged setting time required of the plaster involved with impressions.

Figure 1:
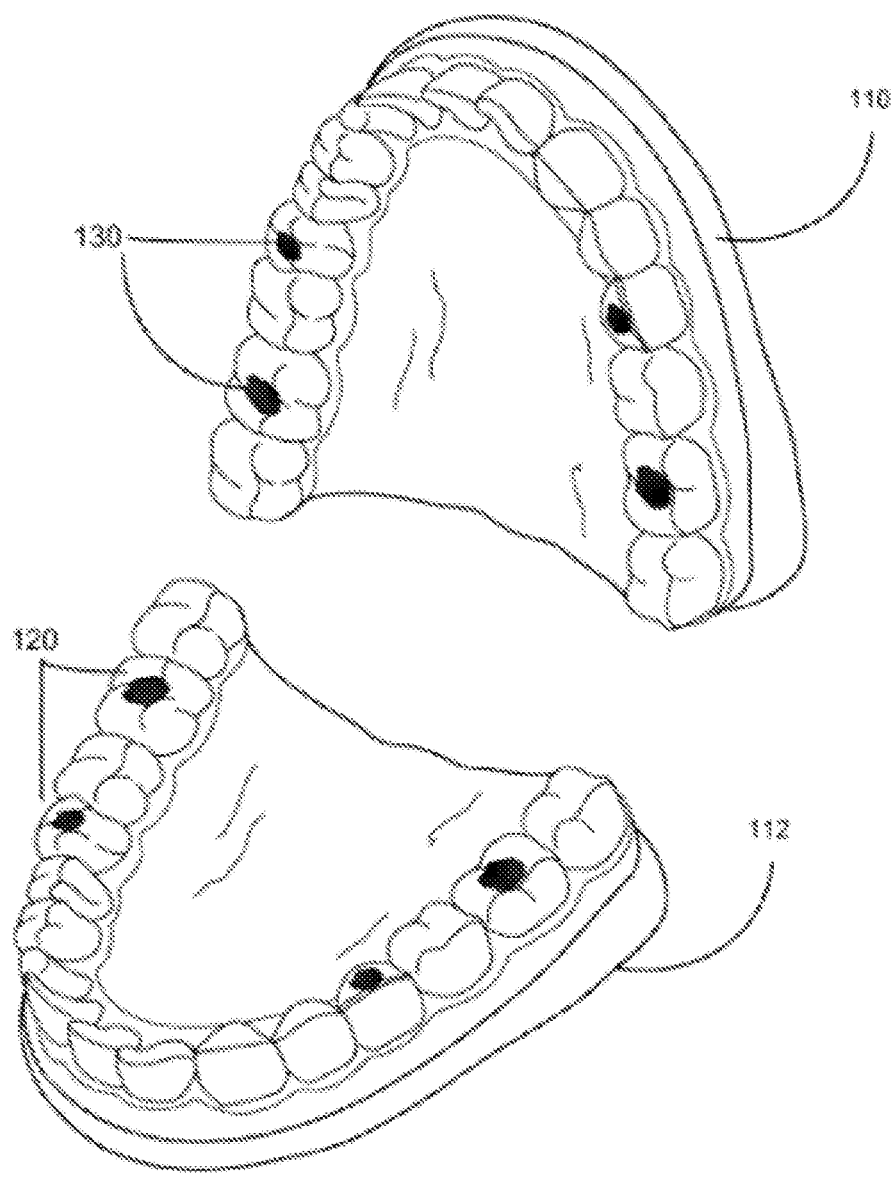
FIG. 1 illustrates a dental mold in accordance with an embodiment of the subject matter of the present application.

The impressions and/or CAD images are used to make a model of the patient's teeth as shown in FIG. 1, items 110, 112. The model is then altered by temporarily attaching a first set of retention hooks to the model of the patient's upper teeth, FIG. 7, block 702. The attachment can be by dental wax, glue, such as a polymer glue or Super Glue.

In one embodiment either or both the bite pads and retention hooks are created via CAD images and 3D printed.

Digital dentistry is quickly becoming a staple for dental treatments among discerning dental professionals. 3D printed models are cost-effective for confirming oral topography via intra-oral or impression scans. Several companies now can use machines to create 3D model solutions for making impressions.

Figure 2:
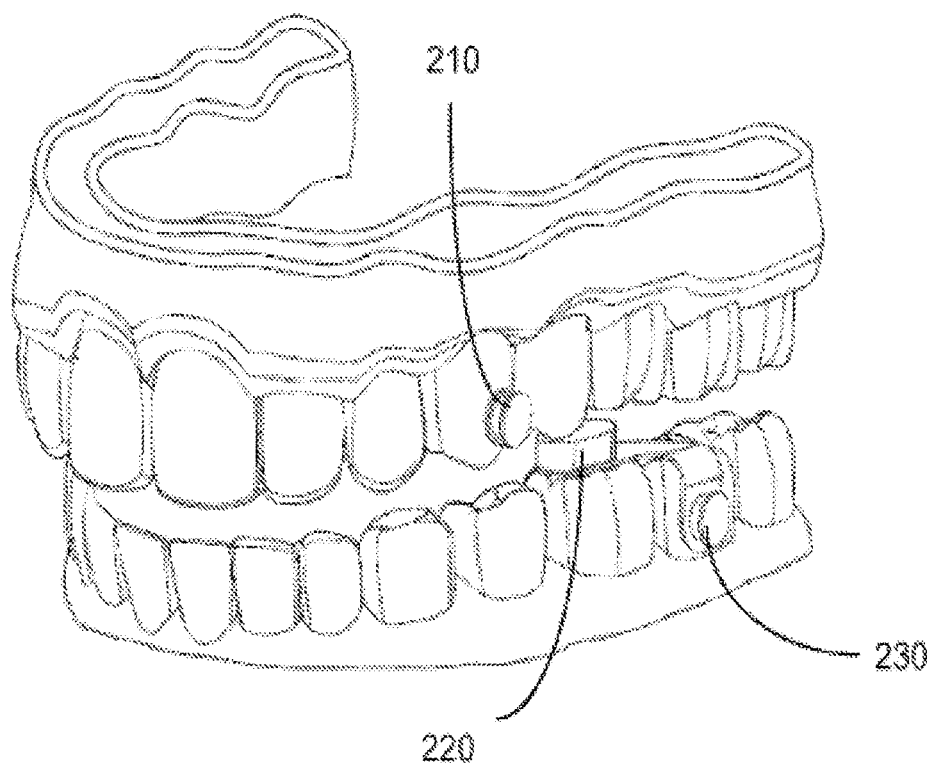
FIG. 2 illustrates a dental mold with bite pads temporarily attached thereon in accordance with an embodiment of the subject matter of the present

The retention hooks which can be 3D printed and patient specific, are placed between the cuspid and first bicuspid on the upper model 210, FIG. 2. Next, with the upper models held in centric occlusion with the lower model, a measuring device applied to the upper retention hook and with a fine point "sharpie" pen scribe a mark on the lower model 23, 25, or 27 mm depending on the size of the patient's dental arch, 120, 130, FIG. 1. According to another embodiment, using CAD images or the like, measuring the placement of the 3D printed retention hooks can be accomplished digitally at 23, 25, 27 mm or other more exact placements.

Figure 3:
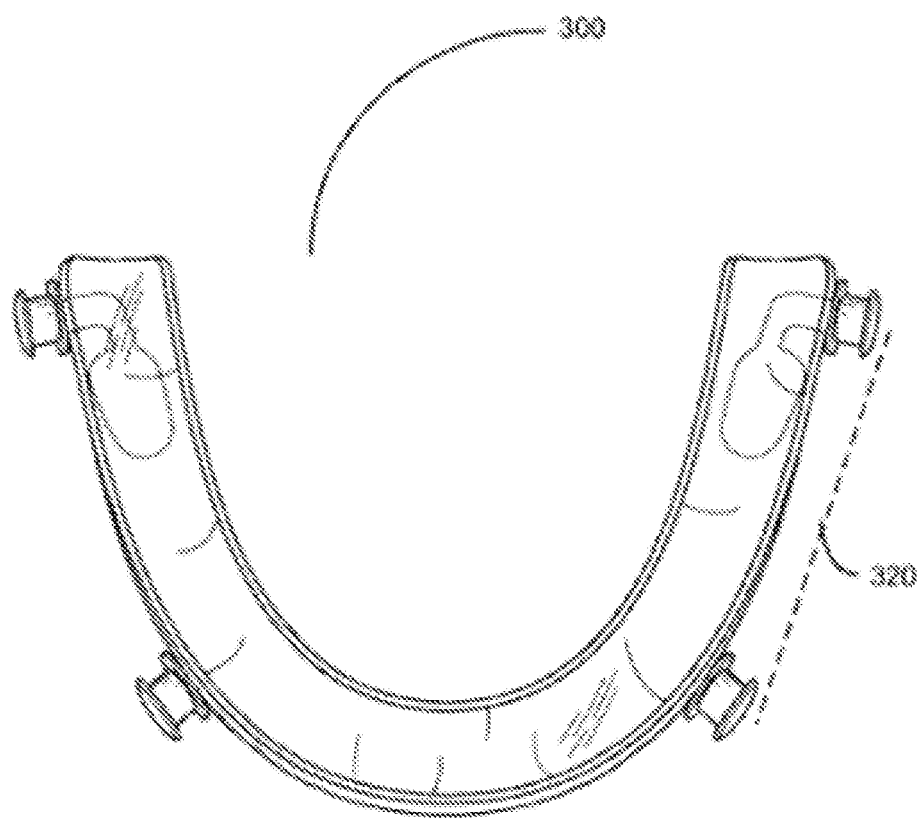
FIG. 3 illustrates a top view of a dental appliance in accordance with an embodiment of the subject matter of the present application.
Figure 7:
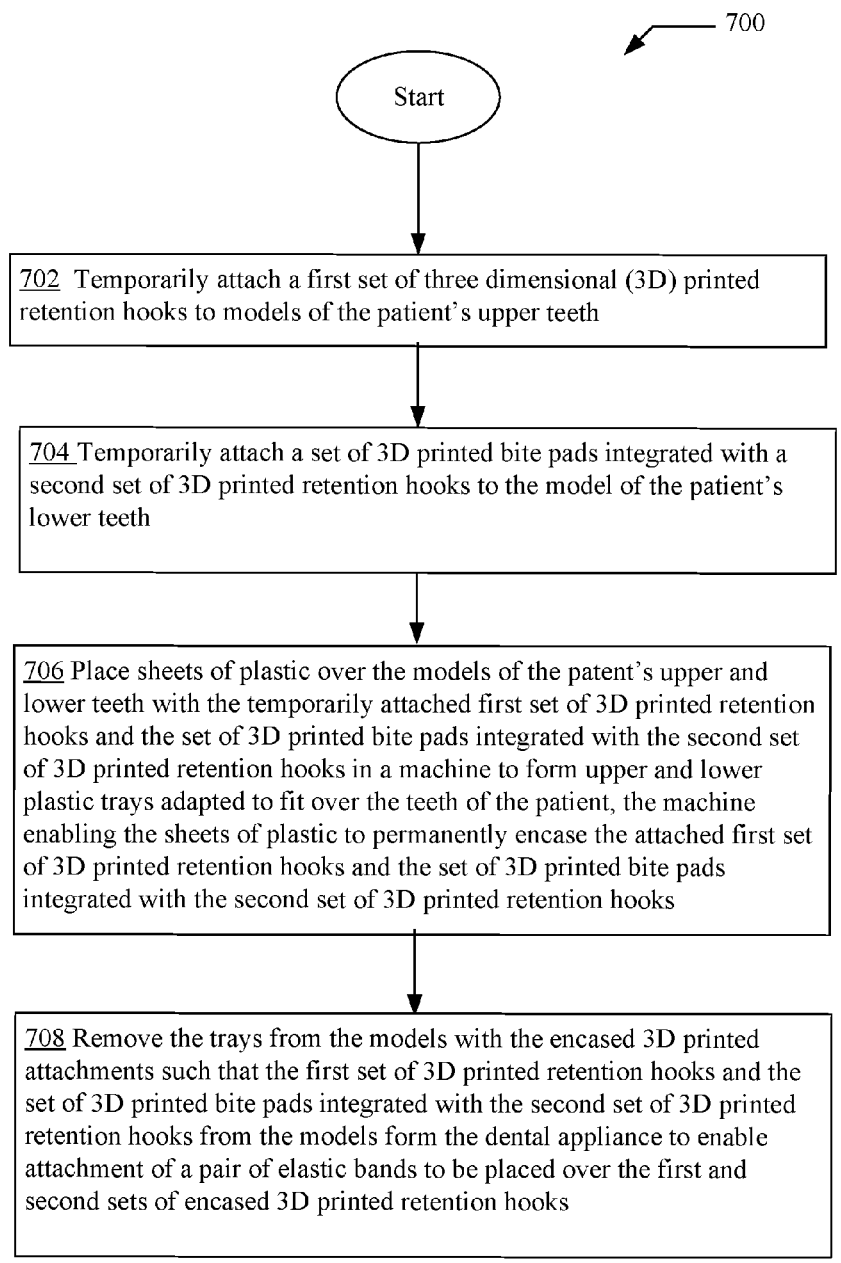
FIG. 7 is a flow diagram illustrating a method in accordance with an embodiment of the subject matter of the present application.

When temporarily attaching the 3D printed lower bite pads integrated with the second set of retention hooks, FIG. 7, block 704, the scribed line (which can be generated automatically via CAD images) on the lower model can be under the center of the second set of 3D printed retention hooks and the top portion of the 3D printed bite pad should be level with the bite pad on the opposite side of the arch. In one embodiment, the lower bite pads integrated with retention hooks shown in FIG. 2 220, 230 are determined via a CAD image(s) and 3D printed. For example, a CAD image can create maximal and minimal measurements for the lower 3D printed bite pads. In one embodiment, the displacement can be 23, 25 or 27 millimeters displaced from the first set of retention hooks 210, measured from center to center, as shown by line 320, FIG. 3 on dental appliance 300.

Likewise, the model, either digital or via plaster, can be altered by temporarily attaching a second set of 3D printed bite pads integrated with a 3D printed second set of retention hooks to the 3D printed model of the patient's lower teeth.

Figure 4:
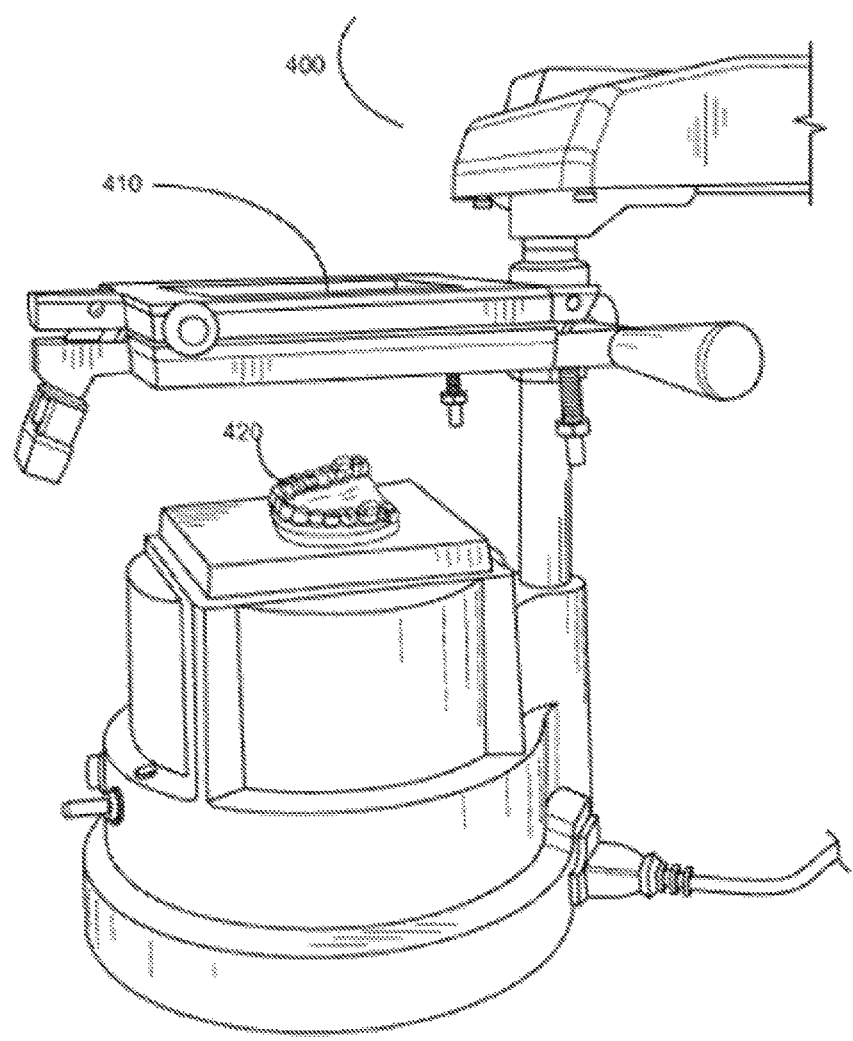
FIG. 4 illustrates a vacuum forming device forming plastic to a dental mold in accordance with an embodiment of the subject matter of the present application.
Figure 5:
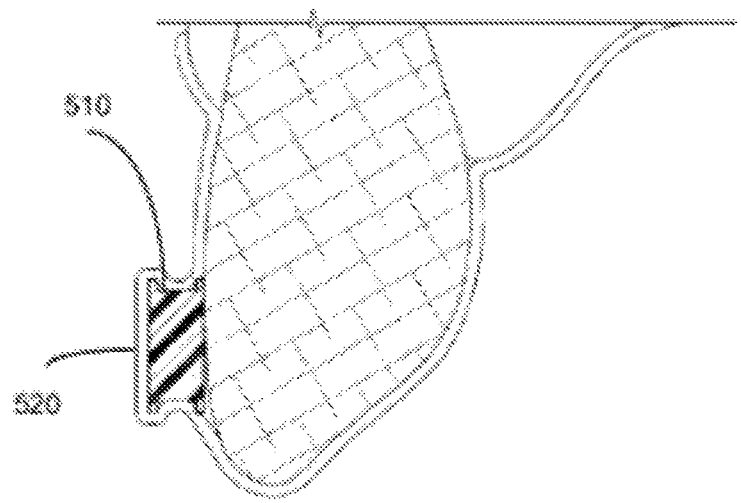
FIGS. 5 and 6 illustrate a retention hook encased in plastic as part of a dental appliance in accordance with an embodiment of the subject matter of the present application.
Figure 6:
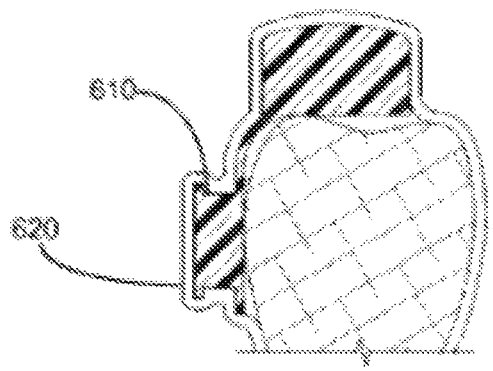

Next, a method employs a machine typically seen in a dentist's office, such as a thermo-plastic machine shown in FIG. 4. According to block 706, FIG. 7, the dentist can place sheets of plastic 410 in the machine 400 so that upon heating and applying vacuum, the sheets are pulled down over the 3D models 420 of the patent's upper and lower teeth with the temporarily attached first set of 3D printed retention hooks as shown in FIG. 5, hook 510, plastic 520 and the set of 3D printed bite pads integrated with the 3D printed second set of retention hooks, as shown in FIG. 6, hook/pad 610 and plastic 620. The machine can operate on the upper and lower teeth models separately, as will be appreciated by those skilled in the art.

The plastic forms upper and lower plastic trays adapted to fit over the teeth of the patient with the 3D printed retention hooks and 3D printed bite pads encased by the plastic. In one embodiment, the 3D printed bite pads are intended to create an 8 mm anterior vertical opening, which can be according to specific patient requirements in accordance with images. Information is obtained from the patient as to any pressures on the teeth or gingiva. Also, the appliance is checked for comfort of and evenness of opening from side to side with the patient. If pressures are felt by the patient on any tooth or any area of the gingiva, then these areas must be carefully relieved. The only reasons there would be pressure on the teeth or gums are the following: (1) inaccurate impression; (2) warped model. In a single office visit, there is generally no concern of intervening tooth movement or dental work since the impression and/or digital imaging was taken on the same visit.

The machine such as a thermo plastic machine, a vacuum forming machine or the like heats the sheets of plastic to encase the temporarily attached first set of retention hooks, right and left, and the set of bite pads integrated with the second set of retention hooks, right and left.

Next, the trays are removed from the models by cutting with scissors, a dental burr, or an exacto knife. The removal of the trays includes the encased first set of retention hooks and the set of bite pads integrated with the second set of retention hooks from the models to form the dental appliance. The vacuum forming over the retention hooks encases the retention hooks and the bite pads.

As shown in block 708, FIG. 7, the appliance created with plastic covering the 3D printed retention hooks and covering 3D printed bite pads enables attachment of a pair of elastic bands to be removably placed over the first and second sets of encased 3D printed retention hooks to create a sleep apnea appliance.

In one embodiment, the encased 3D printed bite pads can be altered by releasably attaching at least two different sizes of snap-on bite pads of one or more thicknesses capable of snapping over the encased right and left 3D printed bite pads to increase the amount of vertical displacement of the lower jaw when the oral appliance is worn.

A doctor or dentist can permanently secure the proper "snap on bite pad" by utilizing a thin mix of orthodontic acrylic or a thin mix of light cure material. Place the prepared mix inside the dry "snap on bite pad", right and left, and then push firmly over the dry incased bite pads right & left. There are two holes for excess material to escape through these holes so the "snap on bite pad" will be properly seated. The lower appliance with its new snap on bite pads on right & left will need to be cured if using acrylic or cured with a light gun.

In one embodiment, a computationally-implemented system for generating a trial oral appliance for sleep apnea, is provided using a three dimensional (3D) printing apparatus coupled to receive one or more digital images of a patient's head, including one or more of upper and lower teeth. The 3D printer produces a 3D printed model of the patient's upper and lower teeth and one or more sets of 3D printed retention hooks, and one or more sets of 3D printed bite pads.

In one embodiment, the 3D printer temporarily attaching a first set of the one or more 3D printed retention hooks to the 3D printed model of the patient's upper teeth. Next, the system temporarily attaches one of the sets of the 3D printed bite pads, wherein the set of the 3D printed bite pad is integrated with a second set of 3D printed retention hooks to the 3D model of the patient's lower teeth.

The 3D printer can be coupled to a vacuum machine such as that shown in FIG. 4 and can be coupled to a 3D printer to automatically place sheets of plastic over the 3D models of the patent's upper and lower teeth with the temporarily attached first set of 3D printed retention hooks and one of the sets of 3D printed bite pads integrated with the second set of 3D printed retention hooks in a machine to form upper and lower plastic trays adapted to fit over the teeth of the patient, the machine enabling the sheets of plastic to permanently encase the attached first set of 3D printed retention hooks and the set of 3D printed bite pads integrated with the second set of 3D printed retention hooks.

In one embodiment the 3D printing system removes the trays from the models with the encased 3D printed attachments such that the first set of 3D printed retention hooks and the set of 3D printed bite pads integrated with the second set of 3D printed retention hooks from the models form a trial dental appliance to enable attachment of a pair of elastic bands to be placed over the first and second sets of encased 3D printed retention hooks.

Referring now to FIG. 7, a flow diagram illustrates a method in accordance with an embodiment. Block 702 provides for temporarily attaching a first set of three dimensional (3D) printed retention hooks to models of the patient's upper teeth. Block 704 provides for temporarily attaching a set of 3D printed bite pads integrated with a second set of 3D printed retention hooks to the model of the patient's lower teeth. Block 706 provides for placing sheets of plastic over the models of the patent's upper and lower teeth with the temporarily attached first set of 3D printed retention hooks and the set of 3D printed bite pads integrated with the second set of 3D printed retention hooks in a machine to form upper and lower plastic trays adapted to fit over the teeth of the patient, the machine enabling the sheets of plastic to permanently encase the attached first set of 3D printed retention hooks and the set of 3D printed bite pads integrated with the second set of 3D printed retention hooks. Block 708 provides for removing the trays from the models with the encased 3D printed attachments such that the first set of 3D printed retention hooks and the set of 3D printed bite pads integrated with the second set of 3D printed retention hooks from the models form the dental appliance to enable attachment of a pair of elastic bands to be placed over the first and second sets of encased 3D printed retention hooks.

As will be appreciated by one of skill in the art, the 3D printer and vacuum machine can be integrated into a system that is computationally controlled with CAD technology and imaging equipment. In one embodiment a method of making a dental appliance for a patient includes retention hooks for moving the lower jaw forward without bite pads. For example, the method includes temporarily attaching a first set of three dimensional (3D) printed retention hooks to models of the patient's upper teeth; temporarily attaching a second set of 3D printed retention hooks to the model of the patient's lower teeth; placing sheets of plastic over the models of the patent's upper and lower teeth with the temporarily attached first set of 3D printed retention hooks and the second set of 3D printed retention hooks in a machine to form upper and lower plastic trays adapted to fit over the teeth of the patient, the machine enabling the sheets of plastic to permanently encase the first set of 3D printed retention hooks and the second set of 3D printed retention hooks; and removing the trays from the models with the encased first set of 3D printed retention hooks and the second set of 3D printed retention hooks from the models to form the dental appliance. The method results in a new oral appliance with permanently encased retention hooks that were once temporarily attached, but via the vacuum forming of the plastic sheets become permanently encased.

While particular aspects of the present subject matter described herein have been shown and described, it will be apparent to those skilled in the art that, based upon the teachings herein, changes and modifications may be made without departing from this subject matter described herein and its broader aspects and, therefore, the appended claims are to encompass within their scope all such changes and modifications as are within the true spirit and scope of this subject matter described herein. Furthermore, it is to be understood that the invention is solely defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

The herein described aspects depict different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality. Any two components capable of being so associated can also be viewed as being "operably couplable" to each other to achieve the desired functionality. Specific examples of operably couplable include but are not limited to physically mateable and/or physically interacting components and/or wirelessly interactable and/or wirelessly interacting components and/or logically interactable and/or logically interacting components.

While certain features of the described implementations have been illustrated as disclosed herein, many modifications, substitutions, changes and equivalents will now occur to those skilled in the art. It is, therefore, to be understood that the appended claims are intended to cover all such modifications and changes as fall within the true spirit of the embodiments of the invention.

What is claimed is:

1. A method of making a dental appliance for a patient comprising:
    three-dimensionally (3D) printing a model of the patient's upper teeth, wherein the upper teeth model includes a temporarily attached first set of 3D printed retention hooks integrated with the upper teeth model;
    3D printing a model of the patient's lower teeth, wherein the lower teeth model includes a temporarily attached set of 3D printed bite pads integrated with a second set of 3D printed retention hooks;
    placing sheets of plastic over the 3D printed models of the patent's upper and lower teeth with the temporarily attached first set of 3D printed retention hooks and the set of 3D printed bite pads integrated with the second set of 3D printed retention hooks;
    vacuum forming the sheets of plastic to form upper and lower plastic trays adapted to fit over the teeth of the patient, the sheets of plastic to permanently encase the attached first set of 3D printed retention hooks and the set of 3D printed bite pads integrated with the second set of 3D printed retention hooks; and
    removing the upper and lower plastic trays from the 3D models with the encased 3D printed attachments such that the first set of 3D printed retention hooks and the set of 3D printed bite pads integrated with the second set of 3D printed retention hooks detach from the 3D models to form the dental appliance and enable attachment of a pair of elastic bands to be placed over the first and second sets of encased 3D printed retention hooks.

2. The method of claim 1 wherein the plastic sheets are approximately three tenths of an inch in thickness.

3. The method of claim 1 wherein the first set of 3D printed retention hooks and the set of 3D printed bite pads integrated with the second set of 3D printed retention hooks include grooved surfaces to enable secure encasement of the sheets of plastic.

4. The method of claim 1 wherein the first set of 3D printed retention hooks are 3D printed between the cuspid and bicuspid teeth of the 3D printed upper teeth model.

5. The method of claim 1 wherein the set of 3D printed bite pads integrated with the second set of 3D printed retention hooks are placed such that the second set of 3D printed retention hooks are displaced backwardly a distance of 23, 25 or 27 millimeters from the first set of 3D printed retention hooks.

6. The method of claim 1 wherein the temporarily attaching the first set of 3D printed retention hooks and the set of 3D printed bite pads integrated with the second set of 3D printed retention hooks includes measuring to determine appropriate placement of first set of 3D printed retention hooks and the set of 3D printed bite pads integrated with the second set of 3D printed retention hooks.

7. The method of claim 1 further comprising trimming excess plastic from the trays.

8. A method of making a dental appliance for a patient comprising:
    three-dimensionally (3D) printing a model of the patient's upper teeth, wherein the upper teeth model includes a temporarily attached a first set of three dimensional (3D) printed retention hooks;

three-dimensionally (3D) printing a model of the patient's lower teeth, wherein the lower teeth model includes a temporarily attached second set of 3D printed retention hooks;

placing sheets of plastic over the upper teeth model and the lower teeth model;

vacuum-forming the sheets of plastic over the upper teeth model and the lower teeth model, respectively, to permanently encase the first set of 3D printed retention hooks and the second set of 3D printed retention hooks to form an upper tray and a lower tray; and removing the trays from the upper teeth model and the lower teeth model each tray respectively including the permanently encased first set of 3D printed retention hooks and the second set of 3D printed retention hooks to form the dental appliance.

* * * * *

UNITED STATES PATENT AND TRADEMARK OFFICE
CERTIFICATE OF CORRECTION

PATENT NO. : 10,179,063 B2  
APPLICATION NO. : 14/983616  
DATED : January 15, 2019  
INVENTOR(S) : Joseph Lee Frantz and Donald Frantz Page 1 of 1

It is certified that error appears in the above-identified patent and that said Letters Patent is hereby corrected as shown below:

In the Specification

Column 1 at Line 39, the filing date of PCT/US2011/030367 currently reading as "Apr. 21, 2011" should read --March 29, 2011--.

Signed and Sealed this  
Twenty-first Day of May, 2019

Andrei Iancu  
*Director of the United States Patent and Trademark Office*